United States Patent [19]

Cherif-Cheikh

[11] Patent Number: 5,776,107
[45] Date of Patent: Jul. 7, 1998

[54] INJECTION DEVICE

[75] Inventor: Roland Cherif-Cheikh, Issy les Moulineaux, France

[73] Assignee: Delab, Paris, France

[21] Appl. No.: 777,634

[22] Filed: Dec. 31, 1996

[51] Int. Cl.$^6$ ............................................. A61M 5/00
[52] U.S. Cl. ............................................. 604/198; 604/263
[58] Field of Search .......................... 604/198, 195, 604/192, 187, 218, 263, 110

[56] References Cited

U.S. PATENT DOCUMENTS

| | | | |
|---|---|---|---|
| 3,016,895 | 1/1962 | Sein | 128/217 |
| 3,572,335 | 3/1971 | Robinson | 128/217 |
| 3,884,230 | 5/1975 | Wulff | 128/221 |
| 4,233,975 | 11/1980 | Yerman | 128/218 |
| 4,359,044 | 11/1982 | Child | 128/1 |
| 4,774,091 | 9/1988 | Yamahira et al. | 424/426 |
| 4,820,267 | 4/1989 | Harman | 604/60 |
| 4,846,793 | 7/1989 | Leonard et al. | 604/62 |
| 4,850,968 | 7/1989 | Romano | 604/110 |
| 4,994,028 | 2/1991 | Leonard et al. | 604/60 |
| 5,098,389 | 3/1992 | Cappucci | 604/158 |
| 5,151,088 | 9/1992 | Allison et al. | 604/198 X |
| 5,250,026 | 10/1993 | Ehrlich et al. | 604/60 |
| 5,267,972 | 12/1993 | Anderson | 604/192 |
| 5,275,583 | 1/1994 | Crainich | 604/264 |
| 5,279,554 | 1/1994 | Turley | 604/60 |
| 5,284,479 | 2/1994 | de Jong | 604/60 |
| 5,433,711 | 7/1995 | Balaban et al. | 604/192 |
| 5,487,733 | 1/1996 | Caizza et al. | 604/110 |

FOREIGN PATENT DOCUMENTS

| | | | |
|---|---|---|---|
| 0 292 936 A3 | 5/1988 | European Pat. Off. | 37/4 |
| 0 415 504 A1 | 8/1990 | European Pat. Off. | 36/4 |
| 1.168.371 | 12/1958 | France | 1/4 |
| 8901124 | 12/1990 | Netherlands . | |

*Primary Examiner*—John D. Yasko
*Attorney, Agent, or Firm*—Fish & Richardson P.C.

[57] ABSTRACT

The invention features an injection device for injecting a liquid or semi-solid composition into a subject.

8 Claims, 4 Drawing Sheets

INJECTION DEVICE

BACKGROUND OF THE INVENTION

The invention relates to a device for the parenteral administration through a needle of liquid or semi-solid drug compositions wherein the needle is protected before and after the injection.

The parenteral introduction of pharmaceutically active compounds is preferred over oral dosage for many indications, e.g., where the drug to be administered would partially or totally degrade in the gastrointestinal tract, or where there is need for a rapid biological response. The need for extemporaneous preparation of such parenteral compositions is eliminated, or simplified, by the use of pre-filled administration devices in which the liquid to be injected is pre-loaded into the device (e.g., a pre-loaded syringe). Such pre-loaded devices, however, have a number of drawbacks, including the inability to preserve the asepsis or sterility of the needle, as well as the general danger of using an exposed needle. To eliminate these drawbacks, it is necessary to avoid the direct exposure of the needle with the environment both prior to and following injection.

SUMMARY OF THE INVENTION

The invention features a comparatively inexpensive injection device with a needle for parenteral injection of liquid or semi-solid drug compositions into a subject, e.g., a mammal such as a human, wherein the needle is protected both before and after the injection.

In general, the invention features an injection device including a housing, the housing having proximal and distal ends and designed to contain a liquid or semi-solid drug composition; a hollow needle, the needle affixed to the distal end of the housing and extending longitudinally within the housing; a plunger, the plunger arranged to slide within the proximal end of the housing; and a hollow sleeve, the hollow sleeve arranged to cover the needle prior to injection and arranged to retract into the housing during injection; wherein the device is designed such that when the sleeve is pressed against the subject, the sleeve retracts into the housing thereby allowing the needle to penetrate the subject, and when the plunger is forced further into the housing, the drug composition is forced from the housing through the needle and into the subject.

In one embodiment, the device is further designed such that when the drug composition is forced from the housing, the plunger forces the sleeve out of the housing to cover the needle. In a further embodiment, the housing contains the liquid or semi-solid drug composition.

In another embodiment, the device further comprises a septum plunger, the septum plunger slidably arranged within the housing between the plunger and the distal end of the housing. In a further embodiment, the device is further designed such that when the drug composition is forced from the housing, the plunger forces the septum plunger into the sleeve, and the septum plunger forces the sleeve out of the housing to cover the needle. In still a further embodiment, the housing contains the liquid or semi-solid drug composition between the plunger and the septum plunger.

In still another embodiment, the housing contains a liquid and a dry drug composition, where the device is designed to combine the liquid and the dry drug composition prior to injection.

The device can further include a releasable lock to inhibit the movement of the plunger into the housing. The device can also include a removable cap which covers the sleeve. The proximal end of the housing may have a flange and the plunger may also have a flange.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

It is believed that one skilled in the art can, based on the description herein, utilize the present invention to its fullest extent. The following specific embodiments are, therefore, to be construed as merely illustrative, and not limiting.

Figure 1:
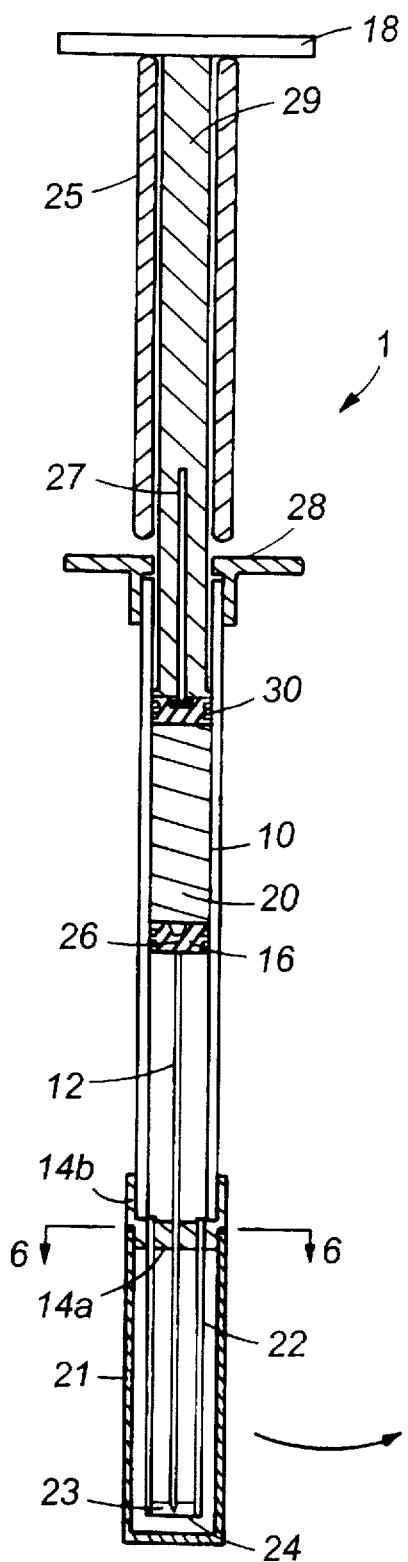
FIG. 1 is a partial cross-sectional view of an injection device prior to use.
Figure 6:
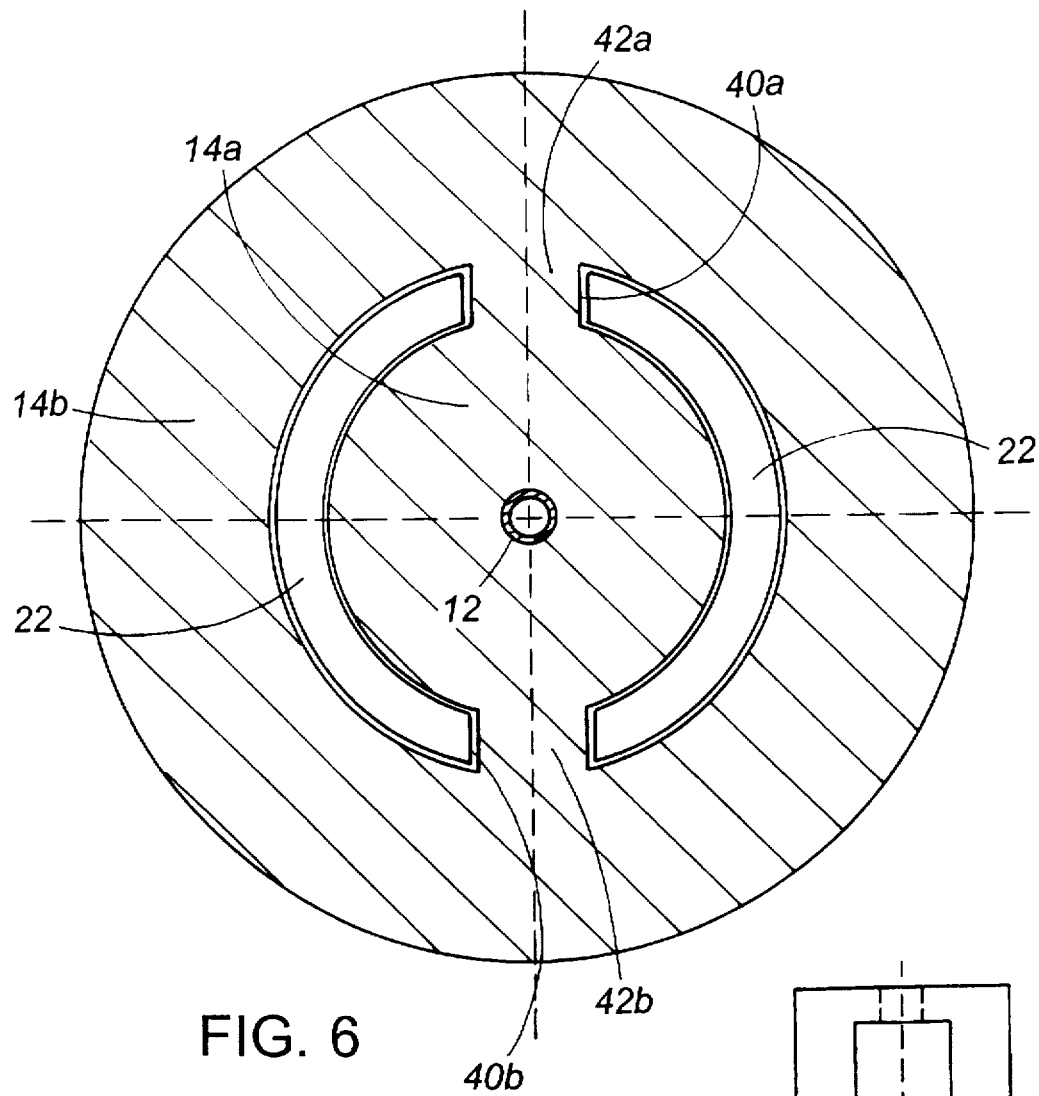
FIG. 6 is a cross-section of the injection device through line 6—6 in FIG. 1.

FIG. 1 shows injection device 1 including housing 10, having a proximal end and a distal end 14a, 14b. The distal end of housing 10 has two holes 40a and 40b partially separating the two parts 14a and 14b of the distal end (as best seen in FIG. 6). Needle 12 is attached to part 14a of the distal end. The housing 10 can be made from a rigid material such as glass, plastic, or metal. The needle 12 is hollow and double-ended, wherein its distal end, remaining outside housing 10, has a point capable of piercing the skin of a subject, and its proximal end, remaining within housing 10, is capable of piercing septum plunger 16. On the proximal end of housing 10 is a flange 28 to assist in removal of device 1 from the subject following injection.

An sleeve 22 surrounds needle 12 so that needle 12 is not fully exposed to the environment until used. Sleeve 22 has longitudinal slots 45a and 45b along its length (see FIG. 7; slot 45b is on the back of the sleeve and is thus not shown). The two parts 14a and 14b of the distal end are joined by radially extending connecting members 42a and 42b (see FIG. 6). Connecting members 42a and 42b, respectively, slide through slots 45a and 45b in sleeve 22, while sleeve 22 slides through holes 40a and 40b in housing 10. Sleeve 22 can be made of suitably rigid material, such as metal, glass, or plastic. Seal 24 covers the opening 23 of sleeve 22 to maintain the sterility of needle 12 and prevent sleeve 22 from unintentionally retracting into housing 10 through holes 40a and 40b prior to injection.

Seal 24 can be made of a thin material, such as plastic or wax, which is easily penetrated by needle 12 during injection. A similar seal can also cover slots 45a and 45b in sleeve 22, to further protect the sterility of needle 12.

Septum plunger 16, contained within housing 10, includes a bore 26, in which needle 12 rests prior to subsequently piercing septum plunger 16. A liquid or semi-solid composition 20 is isolated in housing 10 between the septum plunger 16 and the plunger tip 30, attached to plunger 29. Septum plunger 16 and plunger tip 30 may be made of non-rigid, solid material such as rubber, which allows septum plunger 16 and plunger tip 30 to slide within housing 10 but still maintain sufficient friction with the inner sides of housing 10 to seal composition 20 within housing 10.

The proximal end of plunger 29 has a thumb flange 18 to assist in the depression of plunger 29 into housing 10, and the distal end of plunger 29 has a longitudinal bore 27 to receive needle 12 following injection of composition 20 out and through needle 12. Plunger 29 can be made from a rigid material, such as metal or plastic. A removable lock 25 may be placed between flange 18 and flange 28 to inhibit the further depression of plunger 29 into housing 10 after activation of device 1, i.e., after the housing 10 is filled with a drug composition and the proximal end of the needle is pierced through septum plunger 16. A removable cap 21 can also be used to protect both needle 12 and sleeve 22 prior to use. Both cap 21 and lock 25 can be made from suitable rigid material such as plastic, metal, or rubber.

Figure 2:
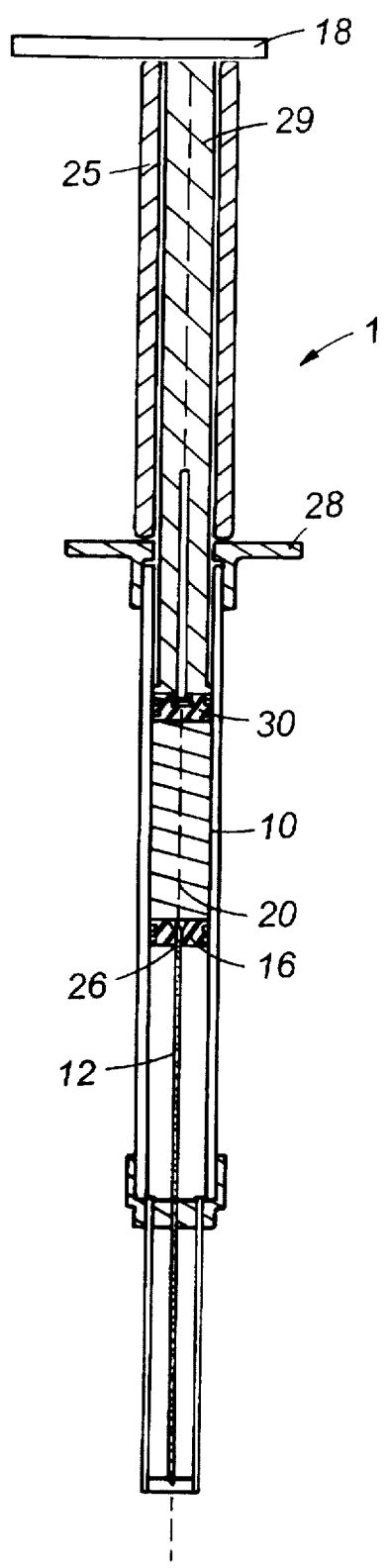
FIG. 2 is a partial cross-sectional view of the injection device of FIG. 1 during use.

FIG. 2 shows device 1 wherein plunger 29 has been pressed into housing 10 to activate device 1 as follows. When plunger 29 is depressed, plunger tip 30, composition 20, and septum plunger 16 are displaced toward the distal end of housing 10. Septum plunger 16 is pierced at bore 26 by needle 12. As a result, the proximal end of needle 12 is exposed to composition 20. Device 1 is now in an activated state. Lock 25, by contacting both flange 18 and flange 28, inhibits the further displacement of composition 20 from housing 10 through needle 12 following activation of device 1, i.e., composition 20 is allowed to fill needle 10, but lock 25 inhibits significant release of composition 20 through needle 10.

Figure 3:
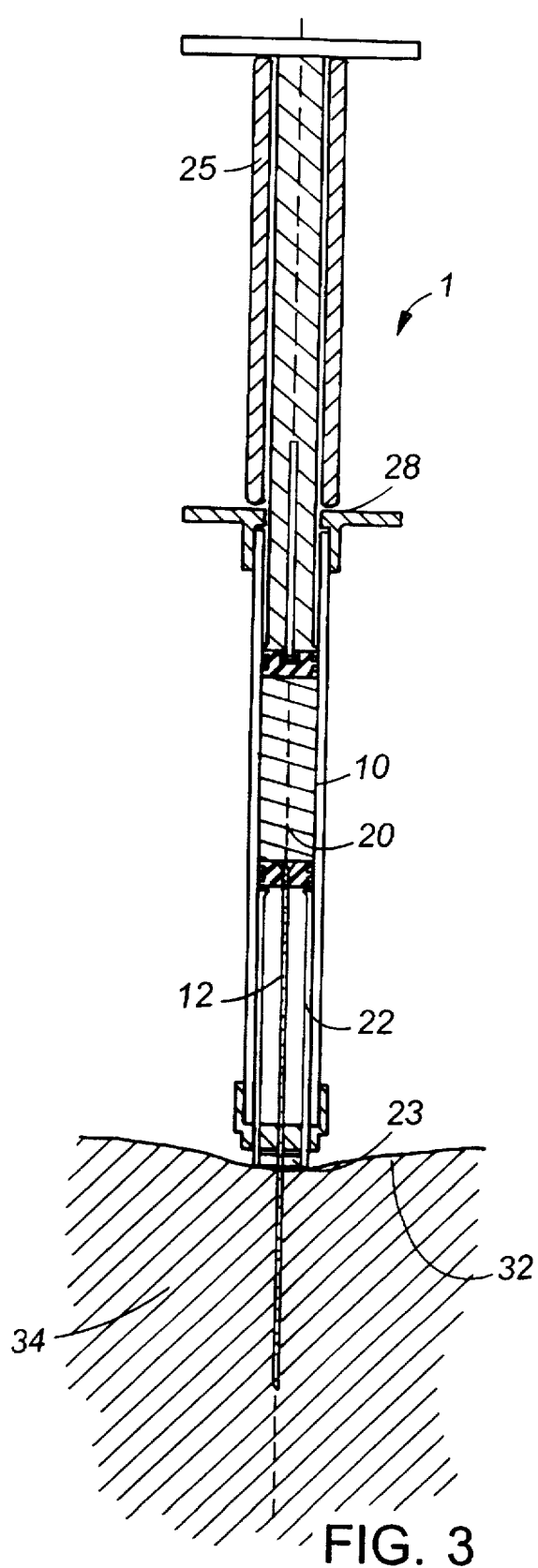
FIG. 3 is a partial cross-sectional view of the device with the needle injected into a subject.

FIG. 3 shows device 1 wherein needle 12 has penetrated skin 32 of the subject being treated. As device 1 is pressed against skin 32, sleeve 22 is retracted into housing 10, through holes 40a and 40b, by the force of pressure against skin 32. Needle 12 passes through sleeve 22 at opening 23. As shown, needle 12 has penetrated through skin 32 into the subcutaneous layer 34.

Figure 4:
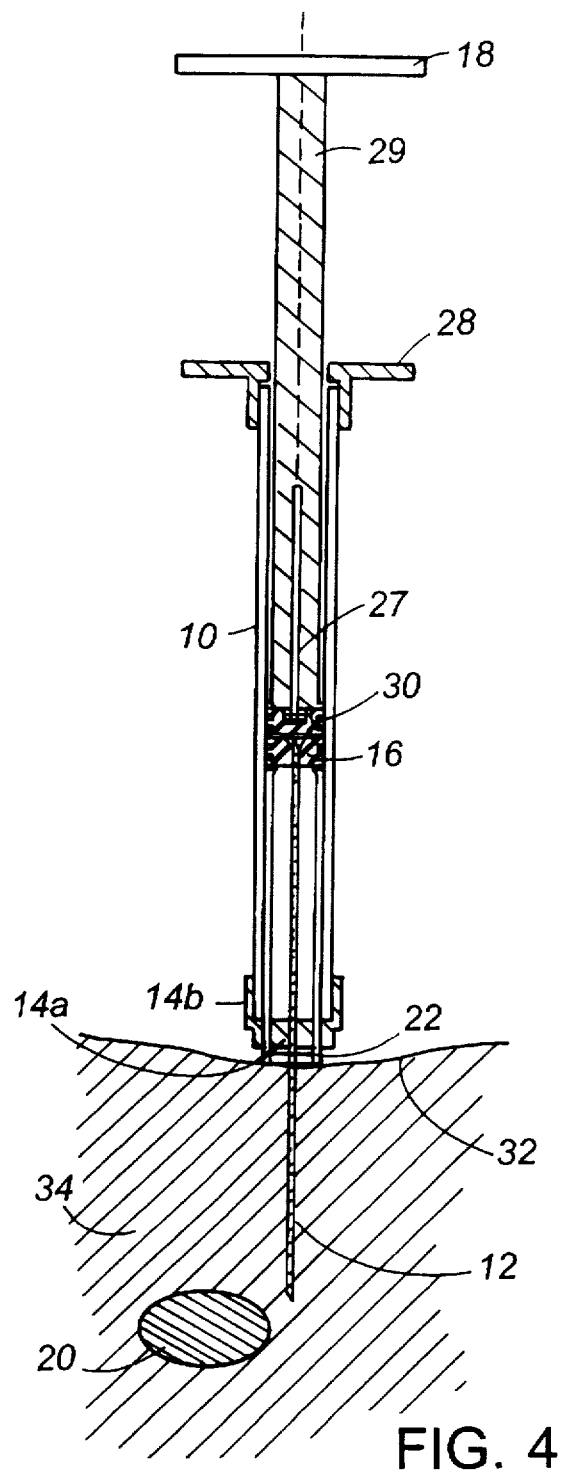
FIG. 4 is a partial cross-sectional view of the injection device being withdrawn from the subject with a drug composition remaining in the subject.

FIG. 4 shows device 1 wherein lock 25 has been removed and plunger 29 has been depressed which moves plunger tip 30 toward septum plunger 16, thereby injecting composition 20 into subcutaneous layer 34 through needle 12. Once composition 20 has been injected and plunger tip 30 rests against septum plunger 16, housing 10 is moved away from skin 32 by exerting pressure against the lower part of the flange 28 while simultaneously exerting opposing pressure on flange 18 of plunger 29. This relative movement of the plunger 29 and housing 10 causes plunger tip 30 to force septum plunger 16 against sleeve 22 as both plunger tip 30 and septum plunger 16 slide toward parts 14a and 14b of the distal end of housing 10, which in turn forces sleeve 22 out of housing 10 through holes 40a and 40b. As plunger tip 30 and septum plunger 16 are moved toward distal end of housing 10, needle 12 penetrates septum plunger 16, plunger tip 30, and enters bore 27 in plunger 29.

Figure 5:
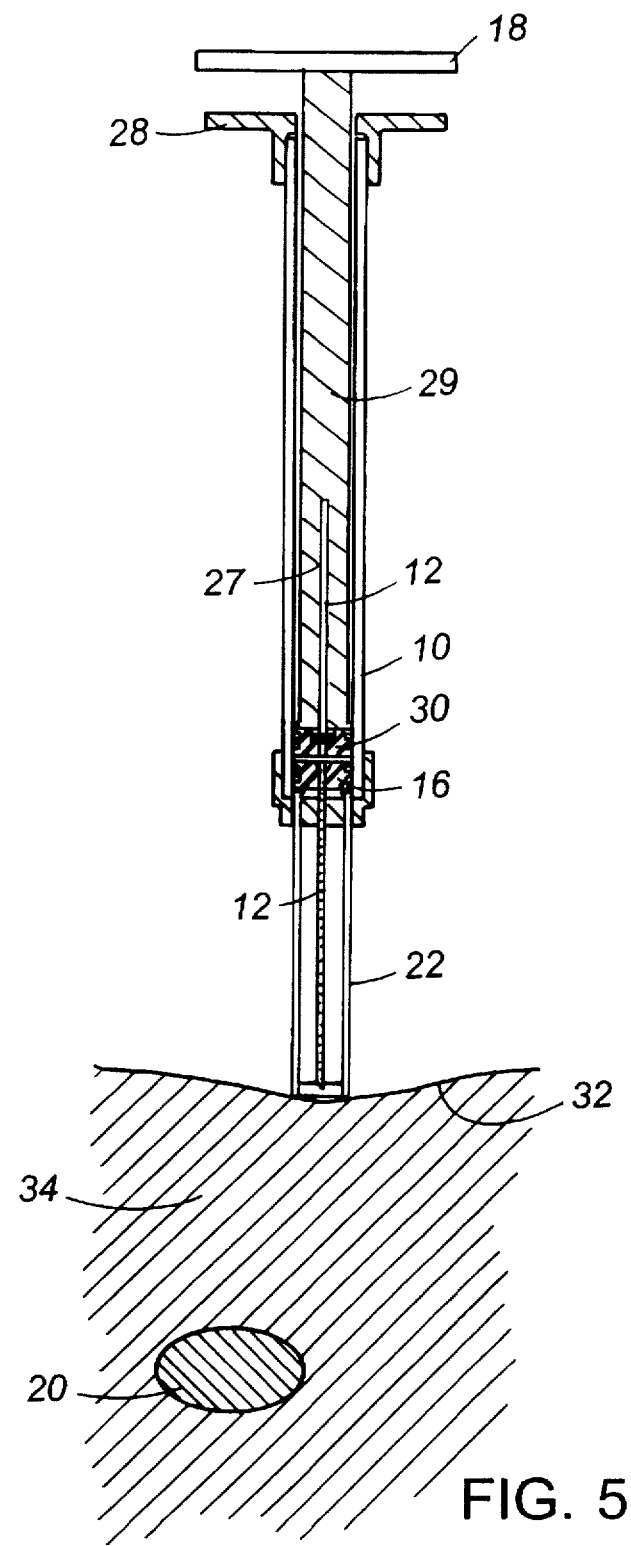
FIG. 5 is a partial cross-sectional view of the injection device following complete withdrawal of the needle from the subject.

FIG. 5 shows needle 12 fully withdrawn from skin 32 and sleeve 22 fully covering needle 12. Composition 20 remains in the subcutaneous layer of the patient. As can also be seen in FIG. 5, the proximal end of needle 12 has been pushed through septum plunger 16 and plunger tip 30 and remains in bore 27 of plunger 29.

Figure 7:
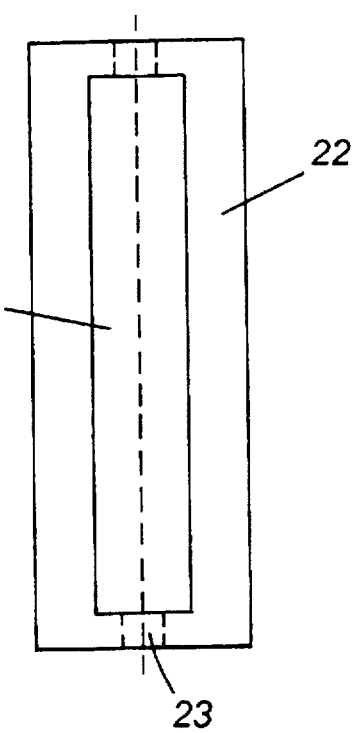
FIG. 7 is a view of the sleeve of the injection device.

FIG. 6 is a cross-sectional view of FIG. 1 at 6—6. FIG. 6 shows holes 40a and 40b in housing 10. Radially extending connecting members 42a and 42b extend through slots 45a and 45b, respectively, to connect parts 14a and 14b of the distal end. Needle 12 is fixed to central part 14a of the distal end, and sleeve 22 can slide through holes 40a and 40b. FIG. 7 shows an isolated sleeve 22 having slots 45a and 45b (45b is not shown but positioned directly opposite to slot 45a on the other side of sleeve 22) and opening 23. Radially extending connecting members 42a and 42b, respectively, slide through slots 45a and 45b.

Composition 20 is a liquid or a viscous semi-solid composition containing a drug. The drug of composition 20 can be any drug capable of being parenterally administered as a liquid or a semi-solid. For example, the drug can be a vaccine, a peptide, a protein, or a small chemical entity. Examples of suitable drugs include insulin and heparin. For drugs which are not stable in liquids over an extended period of time, the liquid and the dry drug can be stored in separate chambers within housing 10. The device can be designed such that the liquid and the dry drug are combined together just prior to injection.

For example, the chamber created between septum plunger 16 and plunger tip 30 (e.g., in FIG. 1) in housing 10 can be separated into two separate parts by a fixed wall or film that can be punctured, e.g., by pressure of the plunger 29 on the plunger tip 30, or a puncturing means. Alternatively, the two parts of the chamber can be separated by a moving wall or septum. In this case, the top or proximal part of the chamber above the moving septum contains the liquid portion of the composition, and the distal part of the chamber contains the solid, e.g., powder, portion of the composition. When plunger 29 is pushed down, it applies pressure to the plunger tip 30, which applies pressure to the liquid portion of the composition. This, in turn, applies pressure on the moving septum, causing it to move in a distal direction. The housing is designed with a liquid bypass (e.g., a bulge or passage in the housing wall) in a location that initially prevents passage of liquid from one part of the chamber to the other, but when the moving septum reaches a specific location, the bypass allows the liquid to pass from the top part of the chamber into the lower or proximal part of the chamber on the other side of the moving septum.

To maintain sterility, the device of the invention can be stored in a conventional blister pack prior to use.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. An injection device for injecting a liquid or semi-solid composition into a subject, the device comprising: a hollow housing having a proximal end and distal end, said housing being configured to contain a liquid or semi-solid composition:

a hollow needle, said needle affixed to the distal end of the housing and extending longitudinally within said housing;

a plunger arranged to slide within the proximal end of the housing;

a septum plunger slidably arranged within the housing between the plunger and the distal end of the housing;

a hollow sleeve slidably connected to the distal end of the housing and arranged to cover the needle prior to injection and to retract into the housing during injection;

wherein the device is configured such that when the sleeve is pressed against the subject, the sleeve retracts into the housing thereby allowing the needle to penetrate into the subject, and when the plunger is pushed into the housing, the composition is pushed from the housing through the needle and into the subject.

2. An injection device of claim 1, wherein the device is further configured such that when the composition is pushed out of the housing, the plunger moves the septum plunger into the sleeve, and the septum plunger pushes the sleeve out of the housing to cover the needle.

3. A device of claim 1, wherein the housing contains the liquid or semi-solid composition between the plunger and the septum plunger.

4. A device of claim 4, wherein the housing contains the liquid or semi-solid composition between the plunger and the septum plunger.

5. A device of claim 1, wherein the device further comprises a releasable lock to inhibit the movement of the plunger into the housing.

6. A device of claim 1, wherein the device comprises a removable cap which covers the sleeve.

7. A device of claim 1, wherein the proximal end of the housing comprises a flange.

8. A device of claim 1, wherein the plunger comprises a flange.

* * * * *